(12) United States Patent
Brenneman

(10) Patent No.: US 10,098,643 B2
(45) Date of Patent: *Oct. 16, 2018

(54) DEVICE AND METHOD FOR ESTABLISHING AN ARTIFICIAL ARTERIO-VENOUS FISTULA

(71) Applicant: ROX Medical, Inc., San Clemente, CA (US)

(72) Inventor: Rodney A. Brenneman, San Juan Capistrano, CA (US)

(73) Assignee: ROX Medical, Inc., San Clemente, CA (US)

( * ) Notice: Subject to any disclaimer, the term of this patent is extended or adjusted under 35 U.S.C. 154(b) by 62 days.

This patent is subject to a terminal disclaimer.

(21) Appl. No.: 15/344,207

(22) Filed: Nov. 4, 2016

(65) Prior Publication Data

US 2017/0071603 A1    Mar. 16, 2017

Related U.S. Application Data

(60) Continuation of application No. 14/593,624, filed on Jan. 9, 2015, now Pat. No. 9,510,832, which is a
(Continued)

(51) Int. Cl.
*A61B 17/11*        (2006.01)
*A61B 17/00*        (2006.01)

(52) U.S. Cl.
CPC ..... *A61B 17/11* (2013.01); *A61B 2017/00526* (2013.01); *A61B 2017/00862* (2013.01);
(Continued)

(58) Field of Classification Search
CPC ............ A61B 17/11; A61B 2017/1107; A61B 2017/1139; A61B 2017/00862; A61B 2017/00526
See application file for complete search history.

(56) References Cited

U.S. PATENT DOCUMENTS 3,538,917 A    11/1970 Selker
3,675,656 A     7/1972 Hakim
(Continued)

FOREIGN PATENT DOCUMENTS

EP    1614400 A2     1/2006
EP    1470785 A1    10/2007
(Continued)

OTHER PUBLICATIONS

"Causes of Erectile Dysfunction", eMedicine Health website, http://www.emedicinehealth.com/causes_of_erectile_dysfuntion/page3_em.htm, May 9, 2007
(Continued)

*Primary Examiner* — Katrina Stransky
(74) *Attorney, Agent, or Firm* — Levine Bagade Han LLP

(57) ABSTRACT

A shunt rivet for implantation in the aorta and inferior vena cava to treat chronic obstructive pulmonary disease, and a method of treating chronic obstructive pulmonary disease. The shunt rivet may be formed to have a central section, a proximal clinch section, and a distal clinch section each having one or more clinch members. These one or more clinch members may be trained to be resiliently biased to bend radially outwardly from the central section.

15 Claims, 7 Drawing Sheets

Related U.S. Application Data continuation of application No. 12/975,013, filed on Dec. 21, 2010, now Pat. No. 8,932,341, which is a division of application No. 10/927,704, filed on Aug. 27, 2004, now abandoned.

(52) U.S. Cl.
CPC .............. *A61B 2017/1107* (2013.01); *A61B 2017/1139* (2013.01)

(56) References Cited

U.S. PATENT DOCUMENTS

| | | | |
|---|---|---|---|
| 3,730,186 A | 5/1973 | Edmunds, Jr. et al. |
| 3,882,862 A | 5/1975 | Berend |
| 4,586,501 A | 5/1986 | Claracq |
| 4,601,718 A | 7/1986 | Possis et al. |
| 4,828,544 A | 5/1989 | Lane et al. |
| 5,108,420 A | 4/1992 | Marks |
| 5,258,042 A | 11/1993 | Mehta |
| 5,491,224 A | 2/1996 | Bittner et al. |
| 5,507,725 A | 4/1996 | Savage et al. |
| 5,756,696 A | 5/1998 | Gray et al. |
| 5,830,222 A | 11/1998 | Makower |
| 5,830,224 A | 11/1998 | Cohn et al. |
| 5,843,170 A | 12/1998 | Ahn |
| 5,944,738 A | 8/1999 | Amplatz et al. |
| 6,053,891 A | 4/2000 | DeCampli |
| 6,099,542 A | 8/2000 | Cohn et al. |
| 6,113,612 A | 9/2000 | Swanson et al. |
| 6,120,534 A | 9/2000 | Ruiz |
| 6,152,937 A | 11/2000 | Peterson et al. |
| 6,168,620 B1 | 1/2001 | Kerr |
| 6,174,681 B1 | 1/2001 | Halling et al. |
| 6,193,734 B1 | 2/2001 | Bolduc et al. |
| 6,231,587 B1 | 5/2001 | Makower |
| 6,309,415 B1 | 10/2001 | Pulnev et al. |
| 6,376,188 B1 | 4/2002 | Halling et al. |
| 6,391,036 B1 | 5/2002 | Berg et al. |
| 6,451,048 B1 | 9/2002 | Berg et al. |
| 6,494,889 B1 | 12/2002 | Fleischman et al. |
| 6,579,311 B1 | 6/2003 | Makower |
| 6,599,303 B1 | 7/2003 | Peterson et al. |
| 6,616,675 B1 | 9/2003 | Evard et al. |
| 6,626,920 B2 | 9/2003 | Whayne |
| 6,669,709 B1 | 12/2003 | Cohn et al. |
| 6,695,878 B2 | 2/2004 | McGuckin, Jr. et al. |
| 6,699,256 B1 | 3/2004 | Logan et al. |
| 6,702,828 B2 | 3/2004 | Whayne |
| 6,746,426 B1 | 6/2004 | Flaherty et al. |
| 6,746,464 B1 | 6/2004 | Makower |
| 6,797,083 B2 | 9/2004 | Peterson |
| 6,858,035 B2 | 2/2005 | Whayne |
| 6,913,607 B2 | 7/2005 | Ainsworth et al. |
| 6,926,690 B2 | 8/2005 | Renati |
| 6,972,023 B2 | 12/2005 | Whayne et al. |
| 6,979,351 B2 | 12/2005 | Forsell et al. |
| 6,985,774 B2 | 1/2006 | Kieval et al. |
| 7,011,094 B2 | 3/2006 | Rapacki et al. |
| 7,056,326 B2 | 6/2006 | Bolduc et al. |
| 7,175,644 B2 | 2/2007 | Cooper et al. |
| 7,182,771 B1 | 2/2007 | Houser et al. |
| 7,303,569 B2 | 12/2007 | Yencho et al. |
| 7,316,706 B2 | 1/2008 | Bloom et al. |
| 7,351,247 B2 | 4/2008 | Kupiecki et al. |
| 7,361,181 B2 | 4/2008 | Hindrichs et al. |
| 7,462,162 B2 | 12/2008 | Phan et al. |
| 7,780,686 B2 | 8/2010 | Park et al. |
| 7,828,814 B2 | 11/2010 | Brenneman et al. |
| 8,088,171 B2 | 1/2012 | Brenneman |
| 8,932,341 B2 | 1/2015 | Brenneman |
| 9,510,832 B2 * | 12/2016 | Brenneman ............ A61B 17/11 |
| 2002/0189727 A1 | 12/2002 | Peterson |
| 2003/0088256 A1 | 5/2003 | Conston et al. |
| 2003/0100920 A1 | 5/2003 | Akin et al. |
| 2003/0187499 A1 | 10/2003 | Swanson et al. |
| 2004/0087984 A1 | 5/2004 | Kupiecki et al. |
| 2004/0087997 A1 | 5/2004 | Brenneman |
| 2004/0211433 A1 | 10/2004 | Albright |
| 2004/0215220 A1 | 10/2004 | Dolan et al. |
| 2004/0220598 A1 | 11/2004 | Bolduc et al. |
| 2004/0249334 A1 | 12/2004 | Cull |
| 2004/0249335 A1 | 12/2004 | Faul et al. |
| 2005/0049675 A1 | 3/2005 | Wallace |
| 2005/0065589 A1 | 3/2005 | Schneider et al. |
| 2005/0107733 A1 | 5/2005 | Faul et al. |
| 2005/0124892 A1 | 6/2005 | Weitzel et al. |
| 2005/0228402 A1 | 10/2005 | Hofmann |
| 2006/0047337 A1 | 3/2006 | Brenneman |
| 2006/0129083 A1 | 6/2006 | Brenneman et al. |
| 2006/0206123 A1 | 9/2006 | Brenneman |
| 2006/0293701 A1 | 12/2006 | Ainsworth et al. |
| 2007/0173867 A1 | 7/2007 | Brenneman |
| 2007/0249985 A1 | 10/2007 | Brenneman et al. |
| 2011/0092877 A1 | 4/2011 | Brenneman |
| 2012/0101423 A1 | 4/2012 | Brenneman |
| 2018/0049742 A1 | 2/2018 | Brenneman et al. |

FOREIGN PATENT DOCUMENTS

| | | |
|---|---|---|
| JP | 01-286478 | 10/2001 |
| JP | 02-529140 | 9/2002 |
| WO | WO 1997/013471 | 4/1997 |
| WO | WO 2001/005463 | 1/2001 |
| WO | WO 2001/072367 | 10/2001 |
| WO | WO 2002/091952 | 11/2002 |
| WO | WO 2004/087236 | 10/2004 |
| WO | WO 2006/026279 | 3/2006 |
| WO | WO 2006/066210 | 6/2006 |
| WO | WO 2006/121855 | 11/2006 |
| WO | WO 2007/005386 | 1/2007 |
| WO | WO 2007/014283 | 2/2007 |

OTHER PUBLICATIONS

"Chronic Obstructive Pulmonary Disease (COPD) Fact Sheet (Chronic Bronchitis and Emphysema)", Feb. 16, 2007, American Lung Association website, www.lungusa.org/site/pp.asp?e=dvLUK9O0E &b=35020.

"COPD: How is COPD Treated?", Feb. 16, 2007, National Heart Lung and Blood Institute Diseases and Conditions Index website, www.nhlbi.nib.gov/health/dci/Diseases/Copd/Copd_Treatments. html.

"Lung—Treatment of COPD and Asthma", Feb. 16, 2007, NLHEP website, www.nlhep.org/lung.trtmnt.html.

Ruebben et al., "Arteriovenous fistulas induced by femoral arterial catheterization: percuntaneous treatment," *Radiology*, 209:729, 1998.

Schlensak et al., "Pulmonary Artery Banding with a Novel Percuntaneously, Bidirectionally Adjustable Device," *Eur. J. of Cardio-thoracic Surg.*, pp. 931-933, 1997.

U.S. Appl. No. 10/927,704, filed Aug. 27, 2004.
U.S. Appl. No. 11/356,876, filed Feb. 17, 2006.
U.S. Appl. No. 11/562,940, filed Nov. 22, 2006.
U.S. Appl. No. 11/696,635, filed Apr. 4, 2007.
U.S. Appl. No. 12/502,120, filed Jul. 13, 2009.
U.S. Appl. No. 12/888,040, filed Sep. 22, 2010.
U.S. Appl. No. 12/975,013, filed Dec. 21, 2010.
U.S. Appl. No. 13/285,860, filed Oct. 31, 2011.
U.S. Appl. No. 13/598,277, filed Aug. 29, 2012.
U.S. Appl. No. 13/973,257, filed Aug. 22, 2013.
U.S. Appl. No. 14/593,624, filed Jan. 9, 2015.
U.S. Appl. No. 14/620,007, filed Feb. 11, 2015.

* cited by examiner

DEVICE AND METHOD FOR ESTABLISHING AN ARTIFICIAL ARTERIO-VENOUS FISTULA

CROSS-REFERENCE TO RELATED APPLICATIONS

This application is a continuation of U.S. patent application Ser. No. 14/593,624 filed Jan. 9, 2015, which is a continuation of U.S. patent application Ser. No. 12/975,013 filed Dec. 21, 2010 now U.S. Pat. No. 8,932,341 issued Jan. 13, 2015), which is a divisional of U.S. patent application Ser. No. 10/927,704 filed. Aug. 27, 2004 (now abandoned), the contents of each of which is incorporated herein by reference in its entirety.

FIELD OF THE INVENTION

The inventions described below relate to treatments for pulmonary hypertension and vascular surgery.

BACKGROUND OF THE INVENTION

Chronic obstructive pulmonary disease (COPD), chronic hypoxia, hypertension, and left ventricular hypertrophy and pulmonary hypertension are diseases of the cardiopulmonary system. Chronic obstructive pulmonary disease (COPD), which includes chronic bronchitis and emphysema, is a slowly progressive lung disease caused primarily by smoking in COPD, the lungs are damaged and the airways are partly obstructed, making, it difficult to breath and leading to a gradual loss of lung function. Symptoms of COPD include chronic cough, excessive sputum production, low blood oxygen levels and severe disabling shortness of breath. COPD represents the fourth leading cause of death in the United States. Chronic hypoxia (reduction of oxygen supply to the body despite adequate blood flow through the body), hypertension, and left ventricular hypertrophy are related conditions which may be symptomatic of COPD or coincident with COPD.

These serious conditions affect many people, and the primary treatments are merely ameliorative. The primary treatments for COPD include avoidance of irritants such as tobacco smoke and breathing supplemental oxygen. In advanced cases of COPD, lung reduction surgery is sometimes performed, but it is not clear that it helps. There is no known cure for COPD.

An aortocaval fistula (ACT) is a rare clinical condition that can be either spontaneous (80% of the cases), related to abdominal aortic aneurysm, or the result of some trauma such as lumbar disk surgery. It is currently seen as a defect that should be cured with surgery and, possibly, stent-graft implantation in the aorta.

Contrary to this understanding, an intentionally formed aortocaval fistula appears to be a viable treatment for COPD. Recently, in our co-pending U.S. patent application Ser. No. 10/820,169 (U.S. Pub. 2004/0249335 A1) filed Apr. 6, 2004, entitled Implantable Arteriovenous Shunt Device and listing John L. Faul, Toshihiko Nishimura, Peter N. Kao & Ronald G. Pearl as inventors (the entirety of which is hereby incorporated by reference), we propose creation of an artificial aortocaval fistula as a treatment for COPD, and we disclose the method of creating the fistula and an implantable shunt for maintaining the aortocaval fistula.

Shunts or steins for connecting blood vessels have been proposed for the treatment of coronary artery disease. Makower, Device, System And Method For Interstitial Transvascular Intervention, U.S. Pat. No. 6,746,464 (Jun. 8, 2004) (tiled Oct. 28, 1998) discloses a stent with a short tubular section spanning the thickness of a coronary artery and an adjacent parallel coronary vein. This stent includes "clovers" on either end of the stent, and these clovers fold radially outwardly to obstruct movement of the stent through the vessel walls. Two clovers on the proximal end of the stent are orthogonal (relative to the radial cross section of the stent) to two clovers on the distal end of the stent, and the interconnecting wires are parallel to the longitudinal axis of the device.

SUMMARY OF THE INVENTION

The devices and methods described below provide for treatment of COPD, hypertension, and left ventricular hypertrophy, and chronic hypoxia. A vascular shunt rivet is disclosed which serves to hold contiguous points of the patient's aorta and inferior vena cava (or other arteries and there associated veins, such as the femoral artery and femoral vein, or the carotid artery and the carotid vein) together and maintain an open flow path from the aorta to the vena cava. The device functions as a rivet, holding the two vessel walls in close proximity, and as a shunt, permitting and maintaining flow from one blood vessel to the other. The device is implanted, between the aorta and inferior vena cava, as a treatment for pulmonary hypertension, COPD and chronic hypoxia.

The shunt rivet is provided in the form of an expandable wire frame structure adapted for transcutaneous delivery and deposit at the desired implantation site. The wire frame structure may be compressed into a small diameter configuration to fit within the distal tip of a delivery catheter. Upon expulsion from the catheter, the wire frame structure resiliently or pseudoelastically expands into a flow-through rivet comprising a tube with expanded heads at either end. When the rivet is released within an artificial fistula formed through the aorta and vena cava walls, it expands to trap the walls between the two expanded heads. The tubular section between the two expanded head may resiliently expand, and may also be balloon-expanded or otherwise plastically deformed to enlarge the flow-through lumen of the tubular section.

DETAILED DESCRIPTION OF THE INVENTION

Figure 1:
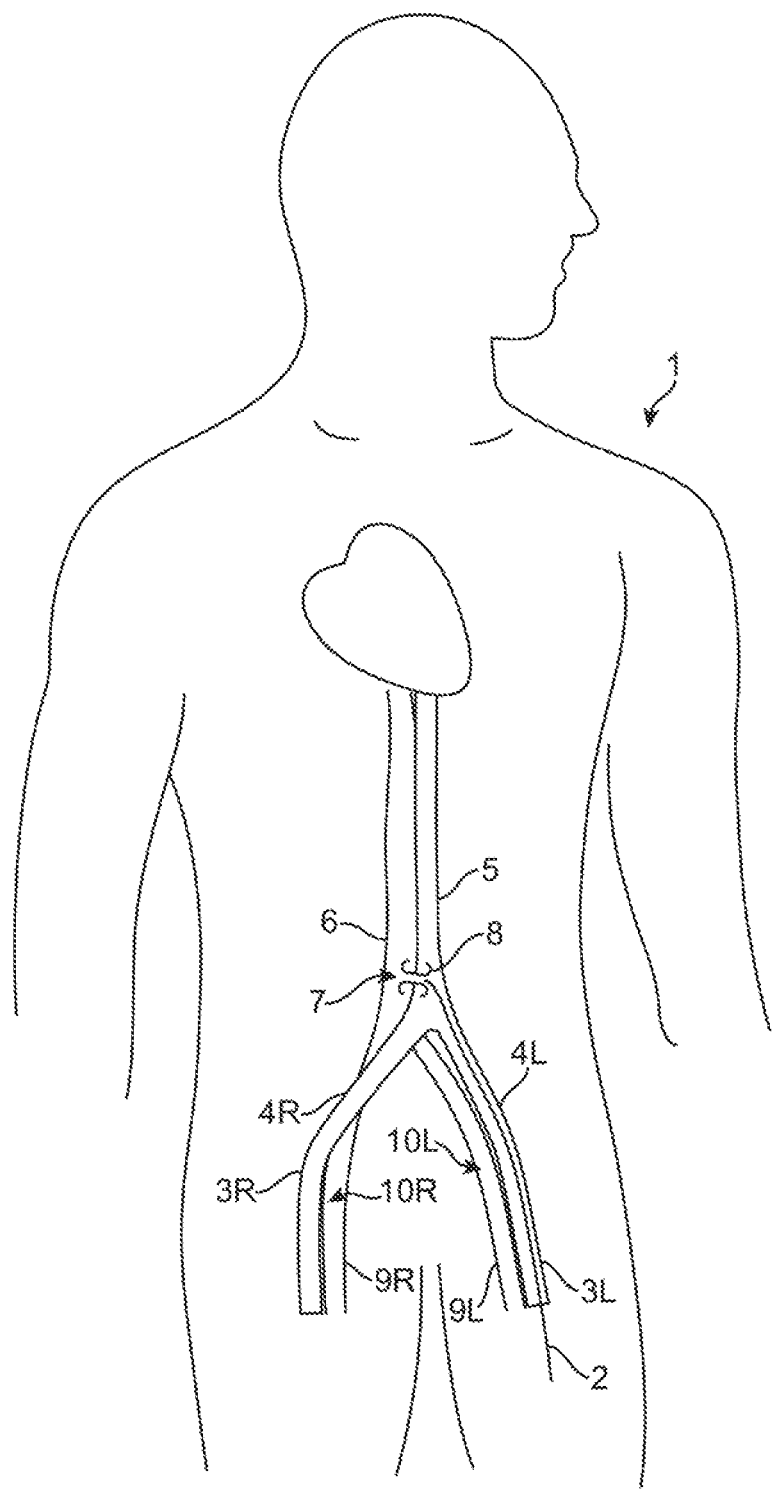
FIG. 1 illustrates the method of installing the shunt rivet to create and maintain an artificial aortocaval fistula.

FIG. 1 illustrates the method of installing, the shunt rivet to create and maintain an artificial aortocaval fistula. The patient 1 is shown with a delivery catheter 2 inserted into the left femoral artery/external femoral artery 3L and pushed upwardly through the left common iliac artery 4L to a point just above the aortic/iliac bifurcation in the distal abdominal aorta 5. The inferior vena cava 6 runs parallel to the aorta, and typically is contiguous with the aorta. As shown in the illustration, the left femoral artery provides a nearly straight pathway to a suitable site of the artificial aortocaval fistula 7 within the abdominal aorta (the right femoral vein 9R also provides a straight pathway to the same site on the vena cava side, and may be also be used as an access pathway). The fistula is created by forming a small hole or slit through the walls of both the aorta and the vena cava at immediately adjacent sites, and is maintained by inserting the shunt rivet 8 described below. The device may also be implanted via a route through the left femoral vein 9L, or through the right femoral artery 3R and/or right common iliac artery 4R, though these pathways are not expected to be so readily navigable. The shunt rivet may also be installed in an artificial arterio-venous fistula formed between the femoral vein and femoral artery on either side of the body, indicated as items 10R and 10L, or between the iliac artery and the femoral vein, and at locations in the aorta above the renal arteries.

Figure 2:
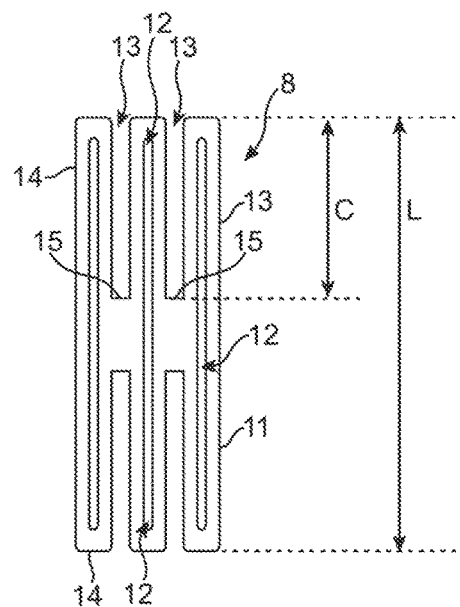
FIG. 2 illustrates an aortocaval shunt rivet in its restrained condition.
Figure 3:
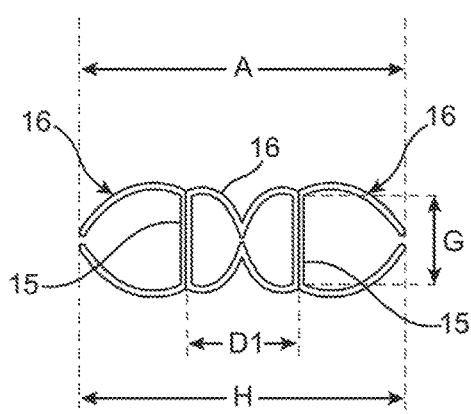
FIG. 3 illustrates the aortocaval shunt rivet of FIG. 2 in a resiliently expanded configuration.

FIG. 2 illustrates the aortocaval shunt rivet 8 in its restrained condition, while FIG. 3 illustrates the aortocaval shunt rivet of FIG. 2 in its resiliently expanded configuration. The shunt rivet may be formed from a single tube 11 of resilient material, such as nitinol, spring steel, glass or carbon composites or polymers, or pseudoelastic (at body temperature) material such as nitinol or comparable alloys and polymers, by laser cutting several closed-ended slots 12 along the length of the tube (leaving, the extreme distal and proximal edges of the tube intact) and cutting open-ended slots 13 from the longitudinal center of the tube through the distal and proximal edges of the tube. The open-ended slots are cut between each pair of closed-end slots to form a number of loops 14 joined at the center section by waist segments 15. Though the shunt rivet illustrated in these figures can be made of several loops of wire welded together at the waist section, and many other fabrication techniques, manufacture from a single tube as illustrated has been convenient.

Figure 4:
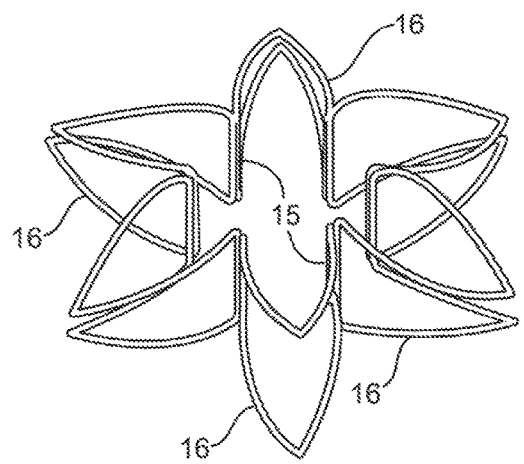
FIG. 4 is a perspective view of the aortocaval shunt rivet of FIG. 2 in a resiliently expanded configuration.

After the tube is cut as described above, it is formed into its eventual resiliently expanded configuration illustrated in FIG. 3. In this configuration, the loops turn radially outwardly from the center section, and evert toward the center plane of the center section, thus forming clinch members 16 in the form of arcuate, everted, petaloid frames at either end of the loop, extending from the generally tubular center section formed by the waist segments 15. For clarity, the term everted is used here to mean that the arc over which the petaloid frame runs is such that the inside surface of the device as configured in FIG. 2 faces radially outwardly from the cylinder established by the tube. FIG. 4 is a perspective view of the shunt rivet in the resiliently expanded configuration illustrated in FIG. 3, more clearly illustrating the relationship between the several petaloid frames at each end of the shunt rivet.

Figure 5:
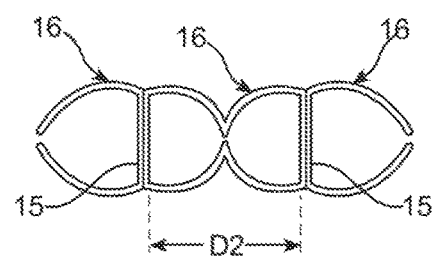
FIG. 5 illustrates the aortocaval shunt rivet of FIG. 2 in a fully expanded configuration.

FIG. 5 shows a side view of the aortocaval shunt rivet of FIG. 2 in a fully expanded configuration. Even after the device has resiliently expanded to the extent possible given its impingement upon the walls of the aorta and the vena cava, the center section may be further expanded by plastic deformation. This may be accomplished by inflating a balloon within the center section, inflating the balloon, and expanding the center section beyond its elastic or superelastic deformation range. By plastically deforming the center section of the shunt rivet, the center section becomes more rigid and able to withstand the compressive force of the walls of the aorta and vena cava.

As illustrated, the construction provides several pairs of longitudinally opposed (that is, they bend to come into close proximity to each other, and perhaps but not necessarily, touch) and aligned (they are disposed along the same longitudinal line) distal and proximal petaloids. Overall, the petaloid frames of the distal section form a "corolla" (analogous to the corolla of a flower) flange or rivet clinch, which impinges on the vena cava wall and prevents expulsion into the aorta, and the petaloid frames of the proximal section form a corolla, flange or rivet clinch (this clinch would be analogous to a rivet head, but it is formed like the clinch after insertion of the rivet), which impinges on the aorta wall and prevents the expulsion of the shunt rivet into the vena cava, and the central section 17 forms a short length of rigid tubing to keep the fistula open. The resilient apposition of the two distal and proximal flanges or corollas so formed will securely hold the shunt rivet in place by resiliently clamping the walls of the aorta and vena cava (even over a considerable range of wall thickness or "grip range").

Referring, to FIGS. 2 through 5, the shunt rivet may be manufactured with an overall initial length L of about 8 to 10 mm to obtain a grip range G of about 3 mm (given a typical aortic wall thickness of 2 mm and a typical inferior vena cava wall thickness of 1 mm at the target site), a clinch allowance C of at least about 3 mm (the clinch allowance is the distally protruding, portion of a rivet that is turned over, curled or flattened to form the formed head), a formed or blind head allowance A of about 10-16 mm (we use the term blind head to refer to the distal head, which is the head that is formed on the blind side of the joint), a head diameter H of 5-16 mm, an initial shank diameter D1 of 3-8 mm (in the resiliently expanded configuration, prior to plastic deformation), a final shank diameter D2 of 5-12 mm to create a flow through lumen of about 5-10 mm diameter. The grip strength of the shunt rivet should provide for a slight compressive force exerted by the opposing clinch members on the intervening blood vessel walls. Thus, the shunt rivet is formed such that, in the resiliently expanded configuration, produces a grip strength in the range of 0.1 to 1.5 oz (about 3 to 45 gram-force) per clinch member upon the intervening blood vessels of the expected thickness.

Figure 6:
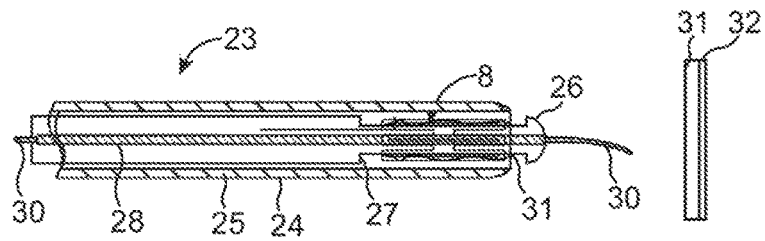
FIGS. 6 through 11 illustrate the deployment of the aortocaval shunt rivet of FIG. 2.

FIGS. 6 through 11 illustrate the method of releasing the shunt rivet so that the distal clinch members are released within the vena cava and the proximal clinch members are released within the aorta. Prior to insertion of the delivery catheter, the surgeon performing the implantation will image the aorta and inferior vena cava with appropriate fluoroscopic, ultrasonic, or other imaging methods, and create it pilot hole in the vessel walls with a crossing catheter. As shown in FIG. 6, the shunt rivet is housed within the distal tip of a delivery catheter 23, and is entirely restrained within the delivery catheter. The delivery catheter includes an outer sheath 24, a shaft 25 which is longitudinally slidable within the outer sheath, and a tapered or rounded tip 26 disposed on the shaft. The tapered may be mounted on a separate shaft, slidably disposed within the shaft 25, so that it may be pushed through the prepared aperture while holding the remainder of the device steady within the aorta. The distal edge of the outer sheath may also be rounded or tapered, as shown. A distally facing shoulder 27 on the shaft, just proximal to the shunt rivet, serves to keep the shunt rivet in place longitudinally as the outer sheath is withdrawn. A guide wire lumen 28 may be provided in the shaft for use with a guide wire 29, and may extend to the proximal end of the shaft for over-the-wire operation or may exit the shaft just proximal to the shunt rivet holding segment for monorail guidewire operation, and other guide wire configurations may also be used. A balloon 30 may be disposed on the shaft (and a suitable balloon inflation lumen provided in the shaft, and a suitable inflation pressure source in fluid communication with the lumen).

Figure 7:
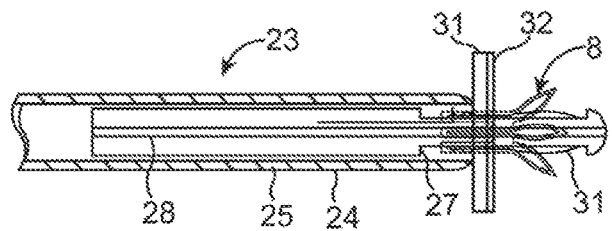
Figure 8:
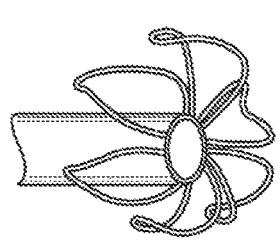

As shown in FIG. 7, the distal tip of the delivery catheter is pushed through a small aperture in the walls of the aorta and vena cava (items 31 and 32) (the aperture is made by the operator, using a separate or integral punch, needle or lance) to create the artificial aortocaval fistula. After the distal tip has entered the vena cava, the outer sheath is pulled proximally to release the distal petaloids, as shown in FIG. 8. After the distal petaloids have reverted to their unrestrained configuration, the entire device is pulled proximally to seat the distal petaloids against the inner wall of the vena cava. Prior to complete release of the shunt rivet, the operator should confirm that its location is acceptable (any suitable imaging technique may be used). To allow retraction in case the shunt rivet must be repositioned, a hook 33 protrudes radially from the shaft 25 and passes through a loop of the shunt rivet. This traps and secures the shunt rivet within the outer sheath 24 until the outer sheath is moved proximally to release the proximal clinch members, so that the operator may pull the shunt rivet back into the outer sheath in case its location, as visualized prior to complete release of the shunt rivet, is undesirable. Any other retaining means, such as a resilient or spring-loaded detent, a retractable pawl which engages a loop of the shunt rivet, of a retractable hook extending inwardly from the outer sheath, may be used in place of the illustrated hook.

Figure 9:
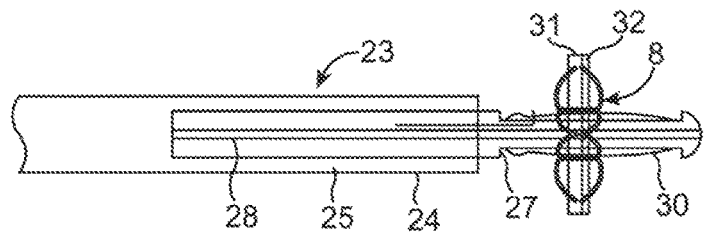
Figure 10:
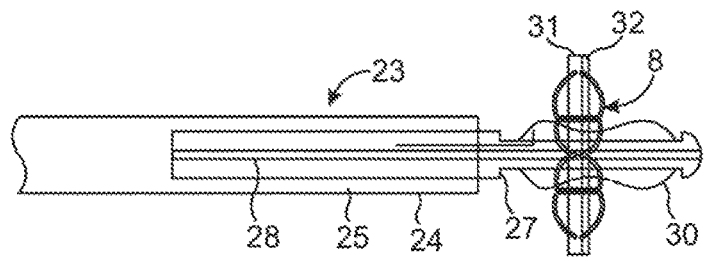
Figure 11:
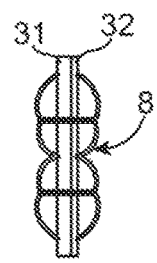

Then the outer sheath is pulled further proximally to release the proximal petaloids, as shown in FIG. 9. With the shunt rivet securely set in the artificial fistula, the center section may then be expanded by inflating the balloon as shown in FIG. 10. Upon withdrawal of the shaft, the shunt rivet remains in place to hold the two perforations in the blood vessel wall in apposition to each other to maintain the fistula, and to maintain an open shunt pathway between the aorta and vena cava, as shown in FIG. 11.

The final form of the shunt rivet is, according to the above description, accomplished with the method that includes forming the generally tubular structure having a central section with a first diameter, a proximal clinch section defined by one or more clinch members, and a distal clinch section defined by one or more clinch members, training the proximal and distal clinch members to make them resiliently biased to bend radially outwardly from the central section; then resiliently compressing the tubular structure to maintain a generally tubular shape and restraining the compressed tubular structure in a compressed configuration suitable for percutaneous insertion into the body; inserting the structure through apposing apertures in the aorta wall and vena cava wall of a patient such that the distal clinch members protrude into the vena cava of the patient and the central section is disposed within the apertures; and then releasing the distal clinch members to permit resilient expansion of the distal clinch members followed by expanding the central section through plastic deformation to larger diameter and releasing the proximal clinch members to permit resilient expansion of the proximal clinch members (the proximal clinch members may be released before or after expansion of the central section).

Figure 12:
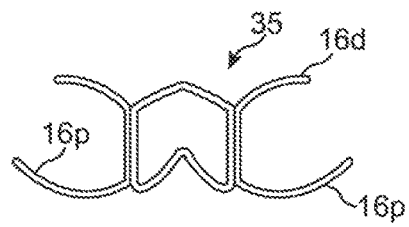
FIG. 12 illustrates an aortocaval shunt rivet with asymmetrically shaped distal and proximal flanges.
Figure 13:
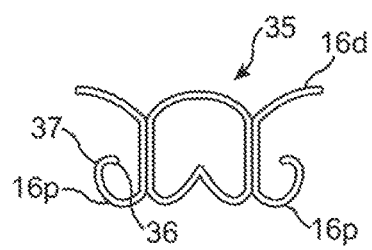
FIG. 13 illustrates an aortocaval strum rivet with asymmetrically shaped distal and proximal flanges.

The shunt rivet illustrated above may be modified as shown in FIGS. 12 and 13, which show an aortocaval shunt rivet with asymmetrically shaped distal and proximal flanges. In FIG. 12, the shunt rivet 35 is similar to the shunt rivet of FIGS. 2 through 4, and includes the central section, the distal flange comprised of multiple petaloid wire-frame members 16d, and the proximal flange comprised of multiple petaloid wire-frame members 16d. In this embodiment, the distal corolla is horn-shaped, "salverform" or "funnelform" (as those terms are used in botany), with the petaloids arcing outwardly without everting (without a substantial arc in the proximal direction), while the proximal corolla, is perianth-like, arcing outwardly and evening with a substantial arc in the distal direction. Each petaloid is significantly reflexed, like the perianth of a narcissus cyclamineus. FIG. 13 illustrates another embodiment of the aortocaval shunt rivet with asymmetrically shaped distal and proximal flanges. In FIG. 13, the proximal petaloids are highly reflexed, and even to form pigtails with an arc of over 180°, and preferably, as illustrated, an arc in excess of about 270°, such that the proximal petaloids bend radially inwardly toward the tips 36 to present a length of wire 37, rather than the tip of the petaloids, for impingement on the blood vessel wall. One or both of the distal or proximal petaloids/clinch members may be modified to form the pigtails illustrated in FIG. 13. In the embodiments shown, the petaloids are gamopetalous with the petals united by their margins, at least at the base, as in FIG. 2 et seq.), but they may also be polypetalous as shown below FIGS. 14, 15 and 16. The embodiments shows are also actinomorphic, though they may be constructed in zygomorphic fashion with asymmetrical petaloids.

Figure 14:
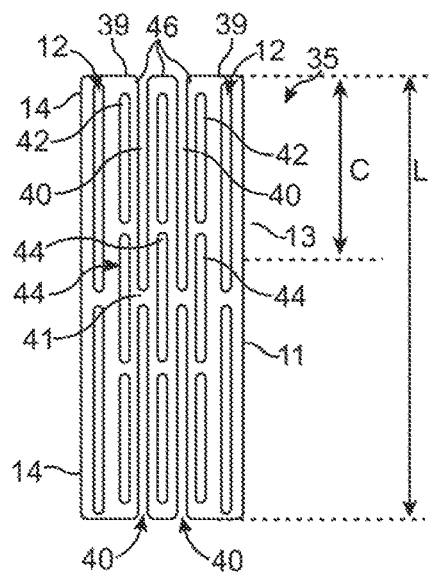
FIGS. 14, 15 and 16 illustrate an aortocaval shunt rivet with strut members that form diamond-shaped cells in the central section upon expansion.
Figure 15:
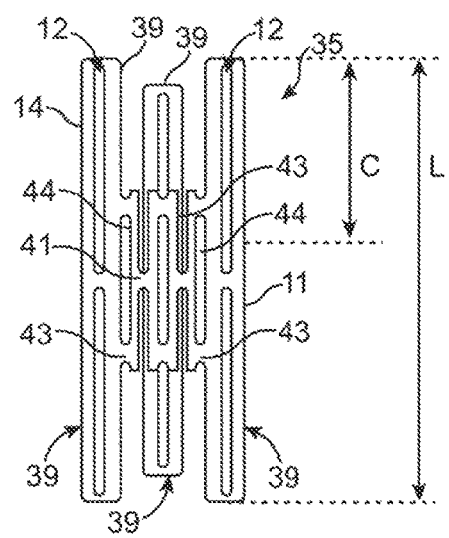
Figure 16:
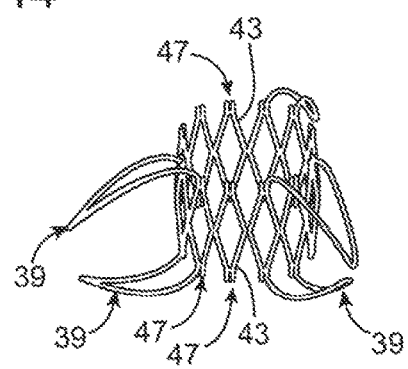

FIGS. 14, 15 and 16 illustrate an aortocaval shunt rivet 8 with diamond shaped strut members in the central section. This shunt rivet provides a central section 17 with a series of expandable loops joined by circumferentially oriented struts 38. FIG. 14 illustrates a tube 11 with numerous slots cut into it to form the shunt rivet shown in FIG. 16. Slots 12 are closed-end slots, leaving a loop 14 extending from the central section 17 to than a clinch member cell 39. Slots 40 are open or closed-end slots extending from the center of the device, leaving small circumferential struts 41 connecting adjacent cells of the device. Slots 42 are open or closed-end slots extending from the center section of the device, leaving larger waist sections 43 connecting the circumferential struts with adjacent clinch member cells of the device. Slots 44 are closed-end slots extending through the waist sections. As shown in FIG. 15, some waste area (segments intended to be removed) 46 shown in FIG. 14 are cut away and Discarded, leaving expandable waist section cells 47 and clinch cells 39, interconnected by the circumferential struts 38. Though the device is illustrated with three clinch members on each end, the number of clinch members formed in the shunt rivet may be varied. The waist section cells and clinch member cells, can, as shown at 48, share struts which define contiguous cells. As shown in FIG. 16 the waist section cells, when expanded, form the diamond shaped cells of the central section. The clinch member cells comprise petaloid cells which may be described as lanceolate (narrow and tapering to an apex (though the apex is preferably blunt)), or ovate (having a broad base and narrow tip) rather than reniform or orbicular. The tip of the petaloid is preferably obtuse, rounded or blunt. As can be appreciated from FIG. 16 the clinch members may also be described as longitudinally extending wires which connect the longitudinally tips of adjacent waist section cells.

Figure 17:
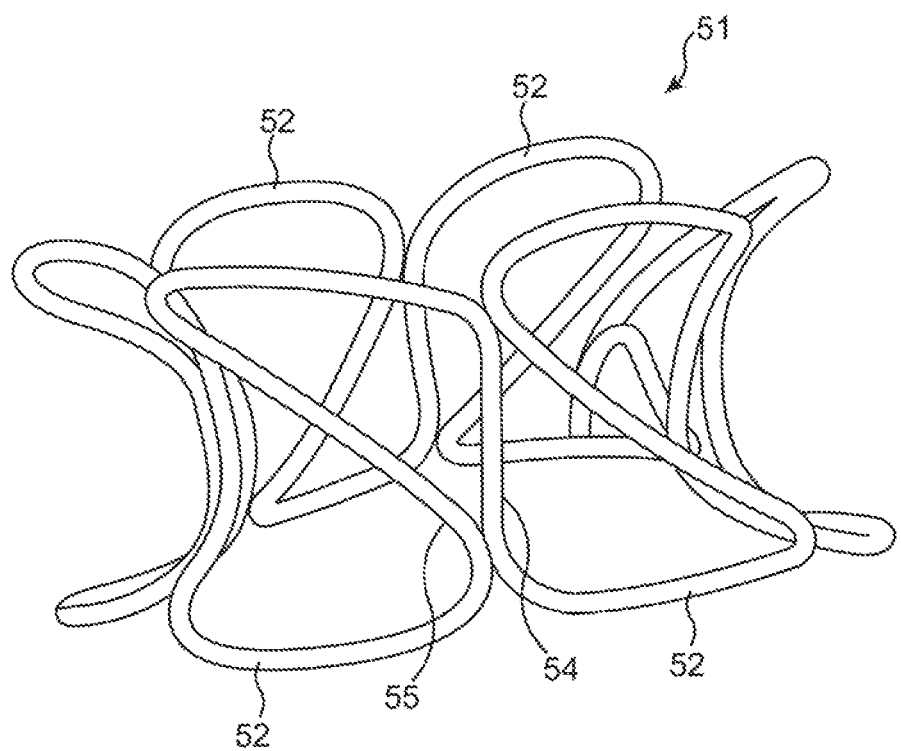
FIGS. 17 and 18 illustrates an aortocaval shunt rivet formed with a single wired wrapped to form the device.
Figure 18:
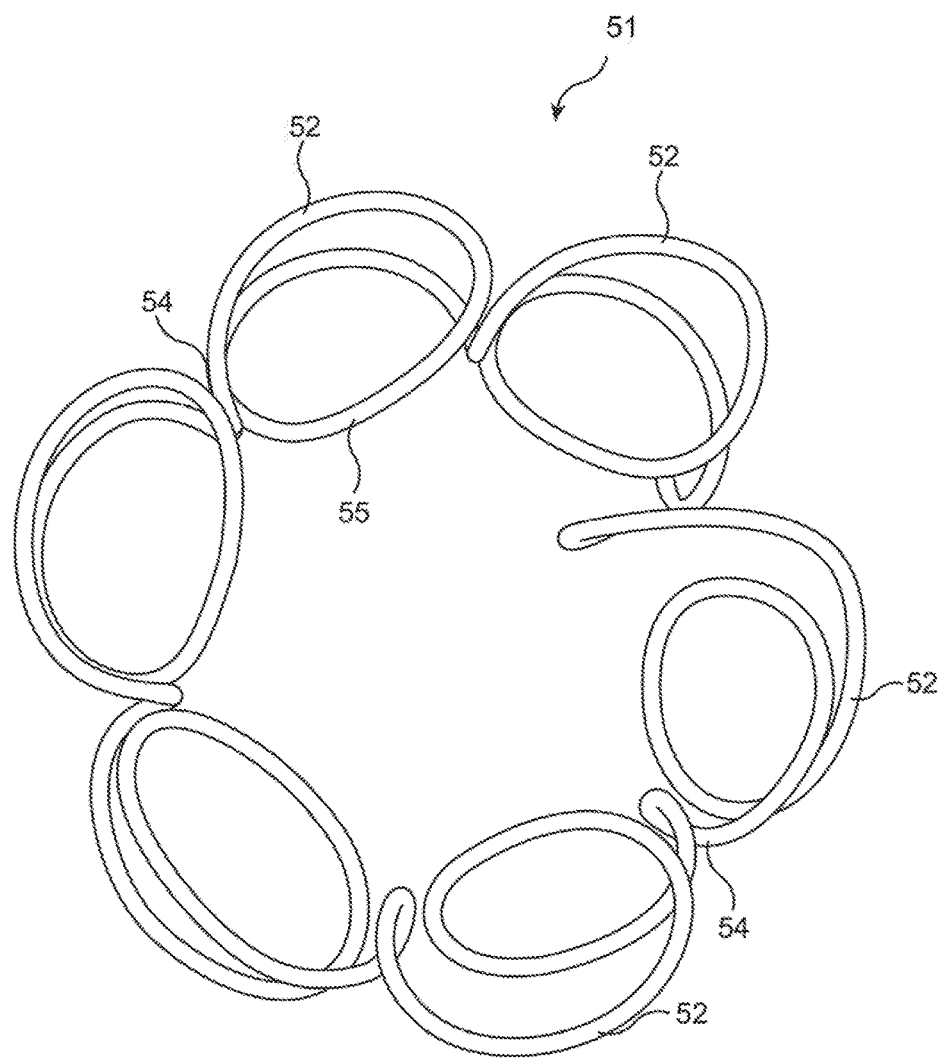

FIGS. 17 and 18 illustrate an aortocaval shunt rivet 51 formed with a single wired wrapped to form the device. In this device, a single wire has been wrapped around a specially formed mandrel to form a number of clinch members 52 on one end of the device and a number of clinch members 53 on the other end of the device. As illustrated, each clinch member is slanted relative to the radius of the device, and the wires forming the waist segment of the device are also oblique to the longitude of the device. As viewed from the top, each cinch member comprises a substantially circular arc, and the wire continues from the arc longitudinally toward the opposite end of the device, forming straight waist segment 54 where it runs substantially parallel to the long axis of the device until it arcs circumferentially away from the previous arc to form the clinch member on the opposite end, whereafter it loops around to extend retrograde relative to the circumference, forming waist segment 55 running obliquely relative to the long axis, and back toward the first end of the device until it curves again circumferentially forward to form the loop of the next clinch member circumferentially adjacent the first loop and longitudinally in line with the immediate previously formed clinch member on the opposite end of the shunt rivet, and continues in this fashion until the entire tubular structure of the device is achieved. En tracing its path, the wire may cross over one or more other portions of the wire.

Figure 19:
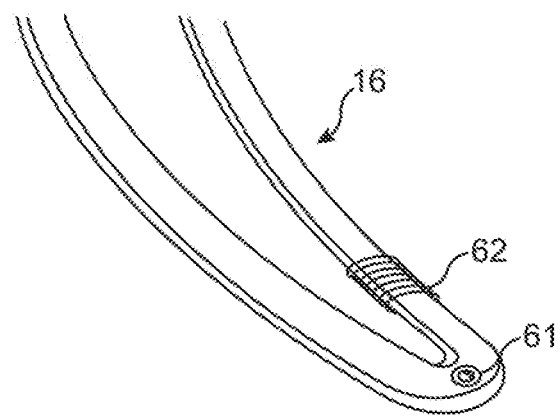
FIG. 19 shows a detail of the clinch member, illustrating radiopaque markers on the shunt rivet.

FIG. 19 shows a detail of the clinch member, illustrating radiopaque markers on the shunt rivet. A radiopaque marker may be provided in the form of a radiopaque rivet 61 disposed near the tip of the clinch member 16, or it may be provided in the form of a wrapped coil of radiopaque wire or thread 62. The radiopaque markers may be comprised of platinum, iridium, tantalum, barium sulfate or other radiopaque materials. Similar markers may also be applied to the waist section. The marker material may also be selected to enhance visibility under ultrasound imaging, magnetic resonance imaging, or other suitable imaging techniques.

Figure 21:
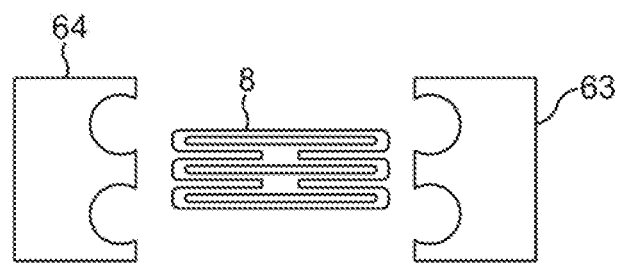
FIGS. 20 and 21 illustrates a mandrel useful for forming and training/heat setting the shunt rivets
Figure 20:
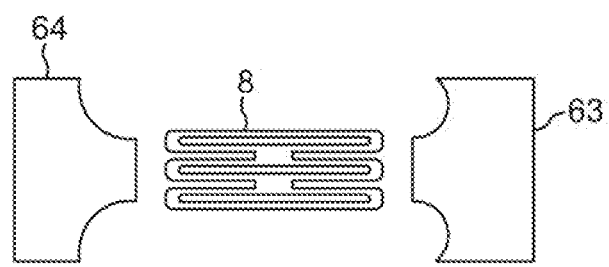

FIGS. 20 and 21 illustrate mandrels or dies useful for forming and training/heat setting the shunt rivets. As shown in FIG. 20, a two part mandrel comprises a distal mandrel portion 63 and a proximal mandrel portion 64. Each mandrel is shaped to correspond to the desired final shape of the shunt rivet and its clinch members. The mandrel portions are inserted into the tube, after it has been cut, so as to deform the device. Where the device is formed from a pseudoelastic material that must be heat set or trained, the mandrels are dimensioned to deform the device to its desired open configuration. Where the device is formed of spring steel or the like, the mandrel is dimensioned to bend the clinch members beyond the desired final configuration. Thus, the mandrel of FIG. 20 and the mandrel of FIG. 21, though shaped differently, may be used to form quite similar shapes for devices made of nitinol and spring steel. The mandrel shapes may be modified as desired to achieve various clinch member shapes, such as the asymmetrical shapes shown in FIGS. 12 and 13.

The devices described above may be provided with coatings or additional structures which serve as matrices for various therapeutic compounds. Drug eluting coatings, additional drug eluting strut members, drug eluting membranes surrounding the central section or drug eluting masses filling the cells of the device may be added to the devices. For the aorto-caval application and the arterio-venous application, therapeutic agents such as heparin and other anti-coagulants and paclitaxol, rapamycin (Sirolumis™), everolimus and other anti-stenotic compounds can be applied to the stent in polymer matrices which permit elution of these drugs over a period of time ranging from several hours to several months after implantation. Polymers such as polyurethane can be used as the matrix.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. A connector device, comprising:
a connector body having a first diameter;
a proximal first member and a distal first member, each being configured to be deployed on opposite ends of the connector body within a first vessel and a second vessel;
a proximal second member and a distal second member, each being configured to be deployed, respectively, opposite the proximal first member and the proximal second member;
wherein the proximal and distal first members and the proximal and distal second members are each configured to be resiliently biased to bend radially outwardly from the connector body and to also produce a grip strength from 3-45 gram-force upon an intervening blood vessel.

2. The device of claim 1 wherein the proximal first member and the distal first member are sized to arc entirely within each respective vessel into a deployed position when the proximal second member and the distal second member contact each respective vessel wall.

3. The device of claim 1 wherein the proximal first member and the proximal second member are configured to arc greater than 270 degrees.

4. The device of claim 1 wherein the distal first member and the distal second member are configured to form a blind head allowance of 10-16 mm.

5. The device of claim 1 wherein the proximal first member and the proximal second member are configured to form a head diameter of 5-16 mm.

6. The device of claim 1 wherein the connector body is a pseudoelastic material, wherein the pseudoelastic material is configured to be pseudoelastic at body temperature.

7. The device of claim 1 wherein the distal first and second members and the proximal first and second members have a deployed configuration longitudinally disposed relative to contiguous portions of the first and second vessels such that the distal first and second members and the proximal first and second members are biased to close upon the contiguous portions.

8. The device of claim 1 wherein the connector body is a resilient material.

9. A method of treating a patient, comprising:
percutaneously positioning a connector body within a first vessel, the connector body having a first diameter, a proximal first member and a distal first member, each being configured to be deployed on opposite ends of the connector body within the first vessel and a second vessel, a proximal second member and a distal second member, each being configured to be deployed, respectively, opposite the proximal first member and the proximal second member; and releasing each of the proximal first and second members and distal first and second members such that the proximal first and second members impinge upon an internal wall of the first vessel and the second vessel with a grip strength from 3-45 gram-forced.

10. The method of claim 9 wherein releasing comprises releasing the proximal first member and the distal first member such that they arc entirely within each respective vessel into a deployed position.

11. The method of claim 9 wherein the distal first member and the distal second member are configured to form a blind head allowance of 10-16 mm.

12. The method of claim 9 wherein the proximal first member and the proximal second member are configured to form a head diameter of 5-16 mm.

13. The method of claim 9 wherein releasing comprises deploying the distal first and second members and the proximal first and second members longitudinally relative to contiguous portions of the first and second vessels.

14. The method of claim 9 further comprising adjusting a diameter of the connector body to alter a flow between the first vessel and second vessel.

15. The method of claim 14 wherein adjusting a diameter comprises increasing or decreasing the diameter of the connector body.

* * * * *